(12) United States Patent
Lorenz et al.

(10) Patent No.: US 7,645,900 B2
(45) Date of Patent: Jan. 12, 2010

(54) PROCESS FOR THE PREPARATION OF ISOCYANATES

(75) Inventors: Wolfgang Lorenz, Dormagen (DE); Matthias Boehm, Leverkusen (DE); Richard Adamson, Leichlingen (DE); Friedhelm Steffens, Leverkusen (DE); Anke Hielscher, Houston, TX (US)

(73) Assignee: Bayer MaterialScience AG, Leverkusen (DE)

( * ) Notice: Subject to any disclaimer, the term of this patent is extended or adjusted under 35 U.S.C. 154(b) by 0 days.

(21) Appl. No.: 12/378,508

(22) Filed: Feb. 17, 2009

(65) Prior Publication Data
US 2009/0209784 A1 Aug. 20, 2009

(30) Foreign Application Priority Data
Feb. 19, 2008 (DE) .................. 10 2008 009 761

(51) Int. Cl.
*C07C 249/00* (2006.01)
(52) U.S. Cl. ....................... 560/352; 560/347
(58) Field of Classification Search .............. None
See application file for complete search history.

(56) References Cited

U.S. PATENT DOCUMENTS

| | | | |
|---|---|---|---|
| 3,226,410 A | 12/1965 | Hettich et al | |
| 3,381,025 A | 4/1968 | Mitsumori et al | |
| 3,544,611 A | 12/1970 | Michelet et al | |
| 4,422,976 A | 12/1983 | Yamamoto et al. | |
| 4,764,308 A | 8/1988 | Sauer et al. | |
| 5,449,818 A | 9/1995 | Biskup et al. | |
| 6,010,612 A | 1/2000 | Freire et al. | |
| 6,149,782 A | 11/2000 | Allen et al. | |
| 6,358,381 B1 | 3/2002 | Allen et al. | |
| 6,402,930 B1 | 6/2002 | Allen et al. | |
| 6,719,957 B2 | 4/2004 | Brady, Jr. et al. | |
| 6,916,953 B2 | 7/2005 | Walsdorff et al. | |
| 2002/0123644 A1 | 9/2002 | Kitai et al. | |
| 2005/0118088 A1 | 6/2005 | Olbert et al. | |
| 2006/0123842 A1* | 6/2006 | Sohn et al. | ..................... 62/617 |
| 2007/0249859 A1* | 10/2007 | Bohm et al. | ................. 560/347 |
| 2007/0293707 A1 | 12/2007 | Wolfert et al. | |

FOREIGN PATENT DOCUMENTS

| | | |
|---|---|---|
| EP | 1849767 A1 | 10/2007 |
| GB | 827376 | 2/1960 |
| GB | 1077031 | 7/1967 |
| JP | 9208589 A | 8/1997 |
| RU | 1811161 A1 | 5/1995 |

* cited by examiner

Primary Examiner—Karl J Puttlitz
(74) Attorney, Agent, or Firm—N. Denise Brown; Nolan J. Cheung

(57) ABSTRACT

The present invention relates to a process for the preparation of isocyanates by reacting the appropriate amines with phosgene, condensing the gas mixture thereby obtained, stripping the liquid phase thereby obtained and returning the solvent so retained in liquid form to the reaction stage. The gaseous constituents are then purified further in an absorption process.

8 Claims, 3 Drawing Sheets

PROCESS FOR THE PREPARATION OF ISOCYANATES

CROSS REFERENCE TO RELATED PATENT APPLICATION

The present patent application claims the right of priority under 35 U.S.C. §119 (a)-(d) of German Patent Application No. 10 2008 009 761.9, filed Feb. 19, 2008.

BACKGROUND OF THE INVENTION

The invention relates to a process for the preparation of isocyanates by reacting the appropriate amines with phosgene, condensing the gas mixture thereby obtained, stripping the liquid phase thereby obtained and returning the solvent so retained in liquid form to the reaction of amine with phosgene. The gaseous constituents are subsequently purified further in an absorption process.

The preparation of isocyanates has been sufficiently known from the prior art for a relatively long time, with phosgene generally being used in a stoichiometric excess, based on the amine or a mixture of two or more amines. Processes for the preparation of organic isocyanates from primary amines and phosgene are described in the literature, for example in Ullmann's Encyclopedia of Industrial Chemistry, 5th ed. Vol. A 19 p. 390 ff., VCH Verlagsgesellschaft mbH, Weinheim, 1991 and G. Oertel (Ed.) Polyurethane Handbook, 2nd Edition, Hanser Verlag, Munich, 1993, p. 60 ff. as well as in G. Wegener et al. Applied Catalysis A: General 221 (2001), p. 303-335, Elsevier Science B. V.

The synthesis of the phosgene used in the amine phosgenation is sufficiently known and is described, for example, in Ullmann's Enzyklopädie der industriellen Chemie, 3rd Edition, Volume 13, page 494-500. Further processes for the preparation of phosgene are described in, for example, in U.S. Pat. No. 4,764,308 and WO-A-03/072237. On an industrial scale, phosgene is mainly prepared by reacting carbon monoxide with chlorine, preferably on activated carbon as the catalyst. The strongly exothermic gas-phase reaction takes place at temperatures of from at least 250° C. to not more than 600° C., generally in tubular reactors. The heat of reaction can be dissipated in various ways. One way to dissipate the heat of reaction is, for example by means of a liquid heat-exchange agent such as those described in, for example, in WO-A-03/072237, or by vapor cooling via a secondary cooling circuit, while simultaneously using the heat of reaction to produce steam as disclosed in, for example, U.S. Pat. No. 4,764,308.

In the amine phosgenation, unreacted phosgene is mostly obtained at least partly in gas form together with the hydrogen chloride that is liberated. In the course of the working up of the isocyanate, phosgene and hydrogen chloride components that are still present in the liquid isocyanate-carrying product stream are separated off. In general, the product stream can still contain portions of solvent, inert gases, such as, for example, nitrogen and carbon monoxide, secondary products of the phosgene synthesis, such as, for example, carbon dioxide, and isocyanate which may have been carried along. In order to operate the isocyanate preparation process as economically as possible, it is essential to recover the excess phosgene with minimal losses and feed it to the phosgenation process again in a concentration, in the solvent in question, that is as optimal as possible for the process, as well as to separate off the hydrogen chloride gas obtained stoichiometrically and subject it to a suitable use, the particular uses making different demands on the hydrogen chloride in terms of purity.

Possible uses of hydrogen chloride include, for example, the sale of the aqueous solution (hydrochloric acid) or use of hydrochloric acid in other industrial or chemical processes. One of the most common possible uses of gaseous hydrogen chloride is the oxychlorination of ethylene with hydrogen chloride to give ethylene dichloride. Other preferred procedures include recycling processes for the hydrogen chloride and the return of the chlorine and/or hydrogen to the production process in which the hydrogen chloride is obtained. Such recycling processes include the catalytic oxidation of hydrogen chloride, for example according to the Deacon process, the electrolysis of gaseous hydrogen chloride and the electrolysis of an aqueous solution of hydrogen chloride (hydrochloric acid). WO-A-04/14845 discloses a process for catalytic oxidation according to the Deacon process, and WO-A-97/24320 discloses a process for the gas-phase electrolysis of hydrogen chloride. An overview of electrochemical recycling processes is given in the article "Chlorine Regeneration from Anhydrous Hydrogen" by Dennie Turin Mah, published in "12th International Forum Electrolysis in Chemical Industry—Clean and Efficient Processing Electrochemical Technology for Synthesis, Separation, Recycle and Environmental Improvement, Oct. 11-15, 1998, Sheraton Sand Key, Clearwater Beach, Fla.".

The electrochemical oxidation of an aqueous solution of hydrogen chloride (hydrochloric acid) using a gas diffusion electrode as the cathode is described in WO-A-00/73538 and WO-A-02/18675.

In the electrolysis of aqueous hydrogen chloride according to the diaphragm or membrane process, the hydrochloric acid is used as electrolyte both in the anode chamber and in the cathode chamber. In the electrolysis, chlorine is produced at the anode and hydrogen at the cathode.

The mentioned possible uses of hydrogen chloride make specific demands in terms of purity, and accordingly, determine the purification outlay after separation of the majority of the other components from the phosgene/hydrogen chloride gas stream. Catalytic hydrogen chloride oxidation according to the Deacon process is carried out using a catalyst which requires prepurification of the hydrogen chloride gas from a phosgenation process by means of absorption on a purification bed or the catalytic combustion of solvent residues in the hydrogen chloride (see WO-A-04/014845). In the gas-phase electrolysis of hydrogen chloride using so-called solid electrolyte systems as described in WO-A-97/24320, contamination of the ion exchanger membrane or of the catalytically active material is not permitted, in order to avoid exchange of the units. In the electrochemical oxidation of an aqueous solution of hydrogen chloride using a gas diffusion electrode as cathode, WO-A-02/18675 proposes purifying the hydrochloric acid by means of activated carbon, and optionally, additionally by means of an exchanger resin. For the use of hydrogen chloride gas in oxychlorination, a two-stage condensation can be used to separate off troublesome impurities such as, for example, solvent residues (see U.S. Pat. No. 6,719,957).

An aqueous solution of hydrogen chloride (hydrochloric acid) for use in, for example, the foodstuffs sector requires a correspondingly high degree of purity. This high degree of purity can be achieved, for example, by adsorptive after-purification on an activated carbon bed, as is known from the prior art.

The treatment of the phosgene- and hydrogen-chloride-containing substance streams from the isocyanate preparation according to the prior art is described hereinbelow.

The general aim is to isolate the substance streams phosgene and hydrogen chloride, with secondary components contained therein, such as, for example, solvents, as economically as possible in the required purity, in order to be able to use phosgene or a phosgene solution of the desired concentration in the amine phosgenation again and to supply hydrogen chloride to a suitable use. The processes of condensation, partial condensation, washing, absorption, adsorption and distillation are conventionally used for that purpose, and are described, for example, in EP 1849797 A1.

A partial condensation of phosgene from the process gas can be achieved advantageously in terms of energy under elevated pressure, such as, for example from 10 to 50 bar, by means of cooling water. It is also reported that the solubility of the phosgene in the solvent is thereby increased, which results in an acceleration of the reaction. However, when this process is carried out on an industrial scale, the increased safety precautions with respect to a leakage resulting in the escape of phosgene are to be taken into consideration, as is described in DE-A-3212510.

Phosgenation reaction and working up of the gas phase under elevated pressure is also described in U.S. Pat. No. 3,544,611. The process gas is cooled with water in the range from 10 to 50 bar in order to condense a large part of the phosgene used in stoichiometric excess. A further phosgene depletion in the hydrogen chloride stream requires the use of refrigerating agents. A further economic advantage of amine phosgenation with working up of the process gas at elevated pressure is the saving in terms of refrigerating energy for the phosgene condensation, which allows the operation to be carried out in more concentrated solutions, and likewise constitutes an energy saving. Alternatively, U.S. Pat. No. 3,544,611 describes an embodiment in which hydrogen chloride from the process gas stream is condensed at 33 bar and a refrigerating agent temperature of −20° C. In a preliminary stage, phosgene is thereby condensed, while cooling with water, and separated off. The required purity of the two components is achieved by a distillation/stripping column between the two condensation stages. An inventive advantage of the present invention as compared with U.S. Pat. No. 3,544,611 is the production of a purified solvent stream in the process step of phosgene and hydrogen chloride separation and purification, which can be used directly for the preparation of a phosgene or amine solution.

In DE-A-10260084, reference is made to U.S. Pat. No. 3,544,611 in relation to an increased risk potential in the case of a leakage as a result of this pressurised procedure. It is further noted that, in the described processes, an undesirably high hydrogen chloride concentration is established in the phosgene for phosgenation, and phosgene is also lost with the hydrogen chloride stream (first variant). In the second variant, in addition to the reference of the already mentioned risk potential, reference is also made to the hydrogen chloride liquefaction at low temperatures and high pressures, which is disadvantageous in terms of energy. The hydrogen chloride must, in general, subsequently be evaporated again, with the use of energy, if it is to be further used.

In GB-A-827376, an amine phosgenation is carried out at about 3 bar. When the reaction is complete, excess phosgene and hydrogen chloride that has formed are separated off at the top of a column, at elevated temperature. From the gas phase, phosgene is condensed and the hydrogen chloride is relieved and conveyed away. With such a simple separation, large residual amounts of phosgene in the hydrogen chloride are to be expected, as well as undesirably high hydrogen chloride contents in the recovered phosgene, and therefore, also in the phosgene solution for the amine phosgenation.

Amine phosgenation to TDI and MDI in chlorobenzene is described in U.S. Pat. No. 3,381,025. When the reaction is complete, solvents are distilled off with phosgene and hydrogen chloride, then chlorobenzene and phosgene are condensed and fed to the phosgenation again, while hydrogen chloride, with not inconsiderable residual amounts of phosgene, is fed to phosgene destruction via an absorber. Here too, the phosgene/hydrogen chloride separation in both streams is incomplete, so that phosgene losses via hydrogen chloride result and undesirably large amounts of hydrogen chloride are contained in the phosgene, and ultimately in the phosgene solution, thus promoting disadvantageous amine hydrochloride formation in the amine phosgenation.

The amine phosgenation disclosed in SU-A-1811161 teaches that the phosgene- and hydrogen-chloride-containing process gas stream separated from the liquid solvent/isocyanate product stream still contains 4% phosgene in the hydrogen chloride gas after several condensation and absorption steps, and is drawn off for further purification and use. This gas stream is combined with the waste gas from a phosgene absorber, in which gas streams from the phosgene preparation and streams from the phosgenation that cannot be condensed further are treated. This waste gas stream from the absorber is described as having a content of 4% chlorine. The chlorine and phosgene impurities mentioned in these partial streams indicate that the phosgene preparation process is disadvantageous and that, in accordance with an incomplete phosgene/hydrogen chloride separation, the phosgenation process is capable of being improved. A process step for minimising the circulating solvent (chlorobenzene), analogous to the present publication, is not described.

In EP-A-0570799, a publication relating to amine phosgenation in the gas phase, reference is made to the separation of excess phosgene after condensation of the prepared isocyanate in a manner known per se. This can be effected by means of a cold trap, absorption in an inert solvent (e.g. chlorobenzene or dichlorobenzene) maintained at a temperature of from −10° C. to 8° C., or by adsorption and hydrolysis on activated carbon. The latter variant appears to have no economic value when carried out on a large scale. The hydrogen chloride gas that flows through the phosgene recovery stage can be recycled in a manner known per se in order to recover the chlorine required for the phosgene synthesis.

U.S. Pat. No. 3,226,410 describes a continuous two-stage amine phosgenation process in the liquid phase. A phosgene solution is mixed in stoichiometric excess with an amine solution in a tubular reactor at temperatures up to 90° C. The second stage takes place in a boiler at from 110 to 135° C. The gas phase, consisting of phosgene, hydrogen chloride and solvent portions, is removed at the top of the second stage, condensed in two stages and fed to the phosgene solution container. Non-condensable portions pass into an absorption column, where phosgene still present in the gas stream is absorbed by means of distilled solvent from the liquid phase of the phosgenation and is fed to the phosgene solution container. Portions from the absorption column that have not been absorbed, for the most part hydrogen chloride gas, are fed to a water-operated HCl absorber in which aqueous hydrochloric acid is produced. In contrast to the present invention, U.S. Pat. No. 3,226,410 does not describe in the amine phosgenation, in the phosgene solvent circuit, a process step in which the amount of solvent is controlled, or optimised or minimised, relative to the total amount of phosgene solution.

A chemical separation of hydrogen chloride and phosgene is of lesser importance for large-scale isocyanate preparation, in view of the treatment and working up of the substance streams solvent, phosgene and hydrogen chloride, because of the large amount of bases, for example, that is used, the loss of hydrogen chloride and the large amount of secondary products formed. In EP-A-1020435 and DE-A-1233854, for example, tertiary amines are used as hydrogen chloride acceptors, which are obtained as solids in the form of the hydrochloride. Alkali or alkaline earth salts or oxides are used for this purpose in JP-A-09208589.

The aim of DE-A-10260084 is to obtain hydrogen chloride of maximum purity and pure phosgene from a substance mixture as is conventionally formed in the preparation of isocyanates by reaction of amines with phosgene. This reference describes a process which in principle has four stages, the fundamental stages of which require two separate columns as well as additional units. The process gas from the isocyanate preparation consists predominantly of phosgene, hydrogen chloride, solvent portions and also low boilers and inert substances, carbon monoxide and carbon dioxide being mentioned here as examples. The first process step is the partial condensation of the process gas, which can take place in one or more stages, it being possible to work, depending on the installation pressure, at from 40° C. by means of cooling water to −40° C. with cooling with brine. The partially condensed mixture so obtained is then guided between the stripping part and the rectifying part into the downstream distillation column. In the indicated example with chlorobenzene as solvent, this column is in the form of a bubble tray column with 22 trays in the stripping part and 11 trays in the rectifying part. The column is used to remove hydrogen chloride from the phosgene and is equipped for that purpose with a circulation evaporator (Robert evaporator) and a tubular heat exchanger as top condenser. At a supply temperature of 24.5° C., a bottom temperature of 38° C., a temperature at the top of −9° C. and a pressure at the top of 2.5 bar, the reflux temperature of the partial condensation product at the top of the column is −20° C. Under these conditions, the product removed at the bottom is indicated as having a hydrogen chloride content of 0.01 wt. %, phosgene is given as 89 wt. % and chlorobenzene as 10 wt. %. This stream is fed to the reaction part of the isocyanate synthesis.

Alternatively to the mentioned evaporator in the distillation column, removal of hydrogen chloride can also be carried out by stripping with an inert gas such as nitrogen, the process solvent vapor, phosgene or another gaseous substance or substance to be evaporated from the process waste gas stream that is to be treated.

The portion not condensed in the top condenser of the distillation column, consisting of 74 wt. % hydrogen chloride and 26 wt. % phosgene, is passed at −20° C. into the lower region of an absorption column which is equipped with three charges of wire mesh rings. Chlorobenzene at −25° C. is introduced at the top of the washer, and the heat of solution of the hydrogen chloride in chlorobenzene is dissipated by an intermediate cooler operated at −30° C. At the top of the washer there are obtained vapors which are fed, downstream of a demister, to a top condenser operated at −30° C. Droplets are hereby retained which, together with a small amount of condensed vapors, are fed into the bottom of that absorber or washer. The top of the column is operated at 2.2 bar and −8° C. and the bottom at 6° C. The product removed at the top, downstream of the condenser, has a hydrogen chloride content of 99.5 wt. %, a phosgene content of 0.1 wt. % and a chlorobenzene content likewise of 0.1 wt. %. The product discharged at the bottom contains 19 wt. % phosgene, 78 wt. % chlorobenzene and 3 wt. % hydrogen chloride.

In the example of DE-A-10260084, the gaseous product discharged at the top is after-purified with an activated carbon filter without its being possible to detect phosgene or chlorobenzene residues by GC analysis or IR spectroscopy.

According to the invention, the product discharged at the bottom of the absorber, with the above-mentioned contents of phosgene and hydrogen chloride, is to be fed to a reaction column, a column for phosgene separation or as reflux for working up of the reaction mixture. In the latter case, reference is made to the possibility of not using a vapor condenser for producing the reflux.

DE 10260084 A1 claims the separation and recovery of hydrogen chloride and phosgene or phosgene solution for re-use or further processing, starting from a substance mixture as is obtained in an amine phosgenation. An optimisation of or increase in the phosgene concentration in the phosgene solution, achieved by the process claimed in this invention or a comparable technology without a marked increase in the installation pressure, is not described.

Starting from this prior art, one technical object has been to provide a process for the preparation of isocyanates, which process comprises purifying the stream obtained thereby, containing hydrogen chloride, phosgene and low boilers and inert substances, and with which solvent, phosgene and hydrogen chloride can be obtained again simply and economically with high purities. At the same time, the technical object has been to increase, in a simple and economical manner, the concentration of phosgene in the phosgene solution in the bottom of the absorption and concentration unit (see examples in EP 1 849 767 A1, referred to hereinbelow as absorber for short) at the same pressure and at the same temperature, or to increase further the hydrogen chloride purity of the hydrogen chloride obtained at the top of the absorber, while the concentration of phosgene in the phosgene solution in the bottom of the absorber remains the same, by increasing the amount of washing liquid supplied.

WO 2006/029788 A1 describes a process for separating hydrogen chloride and phosgene, with the required purity of the individual substances, using ionic solvents. In terms of possible savings in the energy field, this method has the disadvantage that, for example, more than one solvent is required in an amine phosgenation process.

As compared with the processes of the prior art, the process according to the invention provides the possibility of reducing the amount of solvent required in the dephosgenated isocyanate stream, which must be separated off during the working up to give the solvent-free isocyanate, by means of a higher phosgene concentration in the solvent carried in the circuit of the process as a whole. This process provides a marked advantage in terms of energy. Alternatively, while the total amount of solvent in the circuit remains the same, the amount of solvent for purifying the hydrogen chloride can be increased further if an appropriately chosen subsequent process so requires. It has now been found that this can be achieved by the process according to the invention.

SUMMARY OF THE PRESENT INVENTION

The process according to the invention is distinguished by the fact that it comprises purification in a column stripping part (also referred to as the stripper) in which, by the introduction of energy, hydrogen chloride and phosgene can be driven off in gaseous form in the lower region of the column (also referred to as stripping), and solvent which has been purified to the greatest possible extent is removed from the bottom of the stripper, and can then be fed to the amine phosgenation process again as solvent both for phosgene and for amine. Upstream of the stripper there are preferably arranged one or more condensation units in which the gaseous stream obtained in step a) of the process according to the invention, containing hydrogen chloride, phosgene, solvent and also low boilers and inert substances, is partially condensed. According to step b), this partial condensation is preferably carried out in one or more steps, the liquid phase obtained therefrom, consisting substantially of solvent, phosgene and hydrogen chloride, being guided to the top of a stripping column and the gaseous stream, containing substantially hydrogen chloride, phosgene, solvent and also low boilers and inert substances, being passed into an absorber (such as that described, for example, in EP 1 849 767 A1, the disclosure of which is herein incorporated by reference). The liquid phase introduced into the stripping column according to step c) is separated into a solvent phase, which is removed at the bottom of the column and has been freed of phosgene residues, and a gaseous stream (gas phase), which is removed at the top of the column and consists substantially of phosgene, hydrogen chloride, solvent (in concentrations of not more than 30 wt. %, based on the weight of the gaseous stream), low boilers and inert substances. For the introduction of energy, the bottom of the stripping column is preferably equipped with a steam-operated circulation evaporator. In order to achieve the required separation of the substances, the column is preferably equipped with a packing or fillers. There are suitable, for example, packings (fabric or metal) or fillers (rings or saddles) made of metal, ceramics or plastics material, as are generally used in distillation technology or absorption technology.

The low-solvent gas phase obtained according to step c) from the top of the stripping column can then be passed, either on its own or together with the gas stream obtained in step b), directly into an absorber (such as is described in EP 1 849 767 A1, the disclosure of which is herein incorporated by reference) in step e), and can preferably first be passed through a partial condensation in one or more steps. Suitable heat exchangers are any appropriate condensers according to the prior art. Where appropriate, freshly prepared gaseous phosgene can either be condensed and dissolved in the absorber together with this stream or can be condensed in a separate phosgene condensation within the phosgene preparation and fed into the bottom of the absorber or passed separately into the reaction part (step f). Any phosgene-containing solvent streams that are obtained from the phosgene preparation, such as, for example, washing liquids, can either be introduced at the top of the stripper or at the bottom of the absorber.

By using the described stripping column it is possible, even before the phosgene absorption in step e), for a large part of the solvent that is present in the stream obtained in step a) containing hydrogen chloride, phosgene, solvent, and low boilers and inert substances, to be separated off as the bottom product in an manner that is advantageous in terms of energy, in a high purity such as is sufficient for use in the preparation of the amine solution and phosgene solution for use in the phosgenation in step a). However, after the partial condensation that is optionally provided downstream of the absorption, more phosgene remains in the gas phase and must be absorbed by a correspondingly increased solvent stream at the top of the absorber. However, the solvent, which is conventionally obtained from the reaction with the gas phase, is then preferably introduced into the absorption column co-currently, solely in gas form, beneath the top of the absorber, if it is not separated off beforehand by a stripping column as described herein. This portion of the solvent, which is subsequently contained in the phosgene solution drawn off at the bottom of the absorption column, is therefore less effective in terms of its activity as an absorbing agent than the solvent introduced counter-currently at the top of the absorber. By means of this effect it is possible to achieve a higher phosgene concentration in the phosgene solution with the same phosgene concentration in the hydrogen chloride stream at the top of the absorption. As a result, the circulating streams for the process solvent in the region of the phosgene absorption and the separation of the solvent from the isocyanate are minimized, and the energy consumption of the process as a whole is thereby minimized. In particular, it should be noted that, because of the stripping column, this is possibly very effective even at low pressures in the vapor system of the phosgenation.

As an alternative to this economic advantage, it is possible by means of the invention, to use an appropriately increased amount of washing liquid for the hydrogen chloride released via the top of the absorber as compared to that in EP 1 849 767 A1, to achieve even higher purity of this gas, which can be advantageous depending on the use of the resultant gas stream (e.g. use in the Deacon process or as food grade HCl). In that case, the amount of solvent reduced by the stripping column can be used, for example, for introduction at the top of the absorber, the original phosgene solution concentration, or the original solvent amount in the amine phosgenation circuit, being retained.

Accordingly, the present invention relates to a process for the preparation of isocyanates. This process comprises the following steps:

a) reacting at least one amine with phosgene in the presence of a solvent, thus forming a liquid stream containing the corresponding isocyanate and optionally solvent, and a gaseous stream containing hydrogen chloride, phosgene, solvent, and low boilers and inert substances;

b) separating the gaseous stream containing hydrogen chloride, phosgene, solvent, and low boilers and inert substances by partial condensation, thus forming a liquid phase and a gaseous phase, wherein the liquid phase which consists substantially of solvent, phosgene and hydrogen chloride is guided to the top of a stripping column, and the gaseous stream which contains substantially hydrogen chloride, phosgene, solvent in concentrations of not more than 30 wt. %, preferably not more than 10 wt. %, based on the weight of the gaseous stream, and low boilers and inert substances;

c) separating the liquid phase introduced into the stripping column in step b) which consists substantially of solvent, phosgene and hydrogen chloride, into a solvent phase and a gas phase, in which the solvent phase is removed in liquid form from the bottom of the stripping column and which has a phosgene concentration of <0.1 wt. %, preferably <0.01 wt. %, particularly preferably <0.001 wt. %, based on the weight of the liquid bottom stream, and the gas phase is removed at the top of the column and contains phosgene, hydrogen chloride, low boilers and inert substances, and solvent in concentrations of <30 wt. %, preferably of <10 wt. %, particularly preferably <5 wt. %, based on the weight of the gas phase;

d) returning the solvent phase formed in step c) to the phosgenation reaction in step a);

e) introducing the gas phase formed in step c) into an absorption, in which the phosgene contained in the gas phase is absorbed in the same solvent as that which was used in the phosgenation reaction in step a), thereby forming a phosgene solution having a phosgene concentration of from 20 to 80 wt. %, preferably from 50 to 80 wt. %, based on the weight of the phosgene solution;

f) optionally mixing the phosgene solution obtained in step e) with additional phosgene to form a concentrated phosgene solution;

and g) returning the phosgene solution formed in step e) or the concentrated phosgene solution formed in step f) to the phosgenation reaction in step a).

The process of the present invention preferably additionally comprises the following further step:

h) combining the gaseous streams formed in steps b), c) and e) to form a hydrogen chloride stream containing phosgene in concentrations of not more than 0.5 wt. %, preferably not more than 0.2 wt. %, particularly preferably not more than 0.1 wt. %, based on the weight of the hydrogen chloride stream.

DETAILED DESCRIPTION OF THE INVENTION

Figure 1:
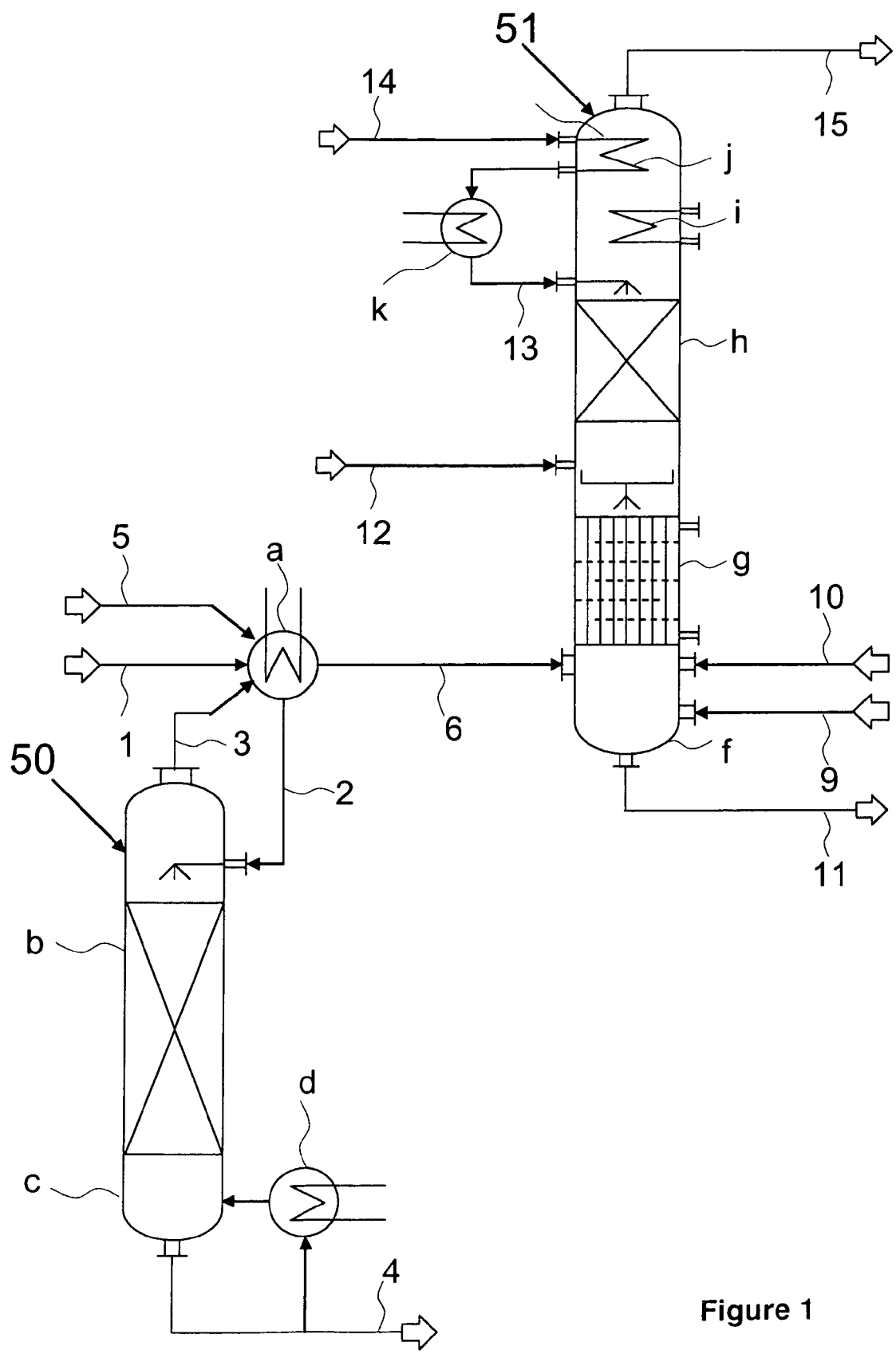
FIG. 1 a diagrammatic representation of the separation of the gaseous stream containing hydrogen chloride, phosgene, solvent, and low boilers and inert substances, in a combination of a single- or multi-stage partial condensation, followed by stripping of the resulting condensation product, and further separation of the vapor stream in an absorption column.

The reaction of amine and phosgene in step a) is preferably carried out in the liquid phase in the presence of a solvent. The term solvent as used herein is understood as meaning organic solvents such as o-dichlorobenzene but not inert gases such as nitrogen or components that boil at low temperatures, such as chloroform. The inert gases are referred to hereinbelow as inert substances and the components that boil at low temperatures (e.g. chloroform) are referred to herein as low boilers.

If the reaction of amine and phosgene in step a) is carried out in the liquid phase in the presence of a solvent, then the same solvent that is used as the solvent in the phosgenation step a) is used as an absorbing agent for the phosgene in step e). The phosgene stream obtained in the absorption column in step f) and depleted of solvent then preferably contains, in addition to the solvent, from 50 to 80 wt. % phosgene, based on the weight of the phosgene solution. This liquid phosgene stream (i.e. phosgene solution) substantially contains solvent and phosgene and can then preferably be returned to the phosgenation reaction in step a) (step g)) without the prior desorption of further phosgene. In order to compensate for the phosgene consumption in the phosgenation reaction in step a), the phosgene solution is preferably mixed beforehand with additional, preferably fresh phosgene. The fresh phosgene can, however, also be added to the amine solution, for example.

If the reaction of amine and phosgene in step a) is carried out in the liquid phase, a liquid stream containing the corresponding isocyanate and optionally solvent is also obtained. This stream preferably contains, particularly when the isocyanate is TDI (toluene diisocyanate) or MDI (di- and polyisocyanates of the diphenylmethane series), less than 75 wt. %, more preferably from 20 to 70 wt. %, and most preferably from 40 to 60 wt. %, based on the weight of the liquid stream, of solvent. This corresponds to a reduction in the content of solvent in the liquid stream of about 10 wt. % solvent, based on the weight of the entire liquid stream, as compared with the conventional liquid phosgenation processes known and described in the prior art, such as those described, for example, in DE-A-19817691.

Finally and preferably there is obtained in step h), from the combination of the gas streams from the stripping column and the phosgene absorber, at the top of the absorber, a purified stream of hydrogen chloride (step h)) containing phosgene in concentrations of not more than 0.5 wt. %, preferably not more than 0.2 wt. %, and more preferably not more than 0.1 wt. %, based on the weight of the hydrogen chloride stream. This purified hydrogen chloride stream which can be fed to further uses.

Separation of the gaseous stream containing hydrogen chloride, phosgene, solvent, and low boilers and inert substances in step b) and the following steps is preferably carried out by first partially condensing phosgene and solvent from the stream containing hydrogen chloride, phosgene, solvent, and low boilers and inert substances (step b)). This liquid stream is introduced as the feed into the top of a stripping column (step c)) and separated into a liquid solvent stream, which has largely been freed of phosgene and is discharged at the bottom of the column as solvent for use in the process again, and a gaseous, low-solvent stream, which is drawn off at the top of the column. Preferably, the gaseous stream obtained in step c) from the top of the column is first fed back into the partial condensation again. The resulting gaseous total stream from the partial condensation, containing hydrogen chloride, phosgene, solvent, and low boilers and inert substances, is then separated in the phosgene absorber, which preferably contains at least one isothermal absorption step and at least one adiabatic absorption step. Alternatively, the gaseous stream obtained in step c) can also be passed directly into the phosgene absorber for carrying out step e).

In a preferred embodiment, the gas stream resulting from the partial condensation in step b), which supplies the feed for the stripping column, is again passed through a partial condensation at a temperature that is preferably below that of the preceding partial condensation carried out in step b), before the resulting gas stream is then separated in the phosgene absorber. As above, it is preferred that the phosgene absorber contains at least one isothermal absorption step and at least one adiabatic absorption step, and the resulting liquid stream is introduced into the bottom of the absorption.

It is also preferred that phosgene-containing solvent streams from the process (e.g. washing liquids from the phosgene preparation, ring liquids from the vacuum system, condensation products from the solvent distillation, etc.) are additionally introduced into the top of the stripping column, and optionally, also into the isothermal absorption step (counter-currently), or optionally, into the bottom of the absorption column.

The isothermal absorption in step e), in which the solvent used in step a) is employed as absorbing agent, is preferably carried out counter-currently. The adiabatic absorption in step e), in which the solvent used in step a) is employed as absorbing agent, is likewise particularly preferably carried out counter-currently.

Following the counter-current adiabatic absorption, residual solvent is preferably condensed from the hydrogen chloride stream. The solvent that has been condensed out is then preferably fed back into the reaction in step a), optionally after being combined with the liquid phosgene stream obtained in step c).

As used herein, absorption is understood as being the uptake and dissolution of gases and vapors in liquids. It is a thermal separation process in which an auxiliary substance, the so-called washing agent, solvent or absorbing agent, is used. The absorbate can be regenerated again by desorption or stripping. The uptake of gas in the solvent (i.e. the absorbing agent) is generally promoted by low temperatures and high pressures; conversely, higher temperatures and lower pressures are to be used in the case of desorption. The absorption of gases in solvents (absorbing agents) is an exothermic operation, that is to say heat is released which, owing to the poorer heat transfer, is transferred only slightly to the gas phase and mainly to the liquid phase. According to Henry's law, the consequence of the rise in temperature of the solvent (absorbing agent) is a reduction in the absorbing capacity of the solvent (absorbing agent) for the substance to be dissolved. In industrial processes, this means a higher solvent requirement while the amount of absorptive is constant. If the heat of absorption is not dissipated or is dissipated only after the absorption has taken place, the term adiabatic absorption is used. If the heat of absorption is removed uniformly during the absorption and the temperature of the solvent is thereby kept substantially constant, the term isothermal absorption is used, which is preferred in practice due to the better utilisation of the solvent (absorbing agent), as already described.

The adiabatic absorption is preferably carried out in fresh solvent (as the absorbing agent), and which corresponds to the solvent used in step a). It has been found to be particularly advantageous in the process according to the invention to absorb the majority of the phosgene contained in the stream containing hydrogen chloride, phosgene and, optionally, solvent, low boilers and inert substances, optionally after partial condensation, by means of an isothermal counter-current absorption in as small an amount of solvent (absorbing agent) as possible, and then to remove residual amounts of phosgene that remain by means of adiabatic counter-current absorption with fresh solvent (absorbing agent) with only a slight adiabatic temperature increase. The optimum outlet concentration of phosgene in the vapor stream (which contains hydrogen chloride, phosgene and, optionally, solvent, low boilers and inert substances) obtained from the isothermal absorption is governed by the amount of solvent (absorbing agent) in the adiabatic absorption and the adiabatic temperature increase that can be tolerated during the adiabatic absorption in view of the absorbing capacity of the solvent (absorbing agent). Adiabatic temperature increases of from 0.1 to 20° C., preferably from 2 to 5° C., have been found to be advantageous here.

Weight ratios of solvent to phosgene at the entry to the isothermal absorption of preferably from 0.1:1 to 10:1, and more preferably from 1:1 to 3:1, are used. All or part of the solvent used for the isothermal absorption can be introduced at the top of the adiabatic absorption.

The design and the operating conditions of the phosgene absorption column in step e) can be chosen such as is described in, for example, EP 1 849 767 A1, which is believed to correspond to U.S. Published Patent Application 20070249859, the disclosure of which is herein incorporated by reference. In other words, suitable operating conditions include a temperature at the top of the phosgene absorption column which is in the range of preferably from −40 to 0° C., and more preferably from −30 to −20° C. The absolute pressure at the top of the phosgene absorption column is preferably from 1 to 35 bar, and more preferably from 1.2 to 3 bar.

In step f), the phosgene solution obtained in step e) can optionally be mixed with additional phosgene to give a concentrated phosgene solution. It is preferred for this step f) to be carried out.

The return of the phosgene solution obtained in step e) and/or of the concentrated phosgene solution obtained in step f) to the phosgenation reaction in step a), which is the subject of step g), can be in such a manner that the entirety of the phosgene solution obtained in step e) and/or the entirety of the concentrated phosgene solution obtained in step f) is returned. It is, however, also possible to return only part of the phosgene solution obtained in step e) and/or of the concentrated phosgene solution obtained in step f). Preferably more than 10%, more preferably more than 50%, most preferably from 60 to 100%, and most particularly preferably from 65 to 99.95%, of the phosgene solution obtained in step e) and/or of the concentrated phosgene solution obtained in step f) is returned to the phosgenation reaction in step a).

The isocyanate preparation by reacting amine with phosgene in step a), i.e. the so-called phosgenation reaction, is conventionally carried out on a large scale in the liquid phase, it being possible for the phosgene and the amine to be dissolved in a solvent. Preferred solvents are chlorinated aromatic hydrocarbons, such as, for example, chlorobenzene, o-dichlorobenzene, p-dichlorobenzene, trichlorobenzenes, the corresponding chlorotoluenes or chloroxylenes, chloroethylbenzene, monochlorodiphenyl, α- or β-naphthyl chloride, benzoic acid ethyl ester, phthalic acid dialkyl esters, diisodiethyl phthalate, toluene and xylenes, as well as methylene chloride, perchloroethylene, trichlorofluoromethane or butyl acetate. Mixtures of the solvents mentioned by way of example can likewise be used. Further examples of suitable solvents are known from the prior art. As is also known and described in the prior art (see e.g. WO-A-96/16028 which is believed to correspond to U.S. Pat. No. 5,925,783, the disclosure of which is herein incorporated by reference), the resulting isocyanate itself can also be used as the solvent for phosgene.

In principle, the phosgenation, and particularly that of suitable aromatic and aliphatic diamines, can also be carried out in the gas phase, that is to say at a temperature above the boiling point of the amine. Gas-phase phosgenation is described, for example, in EP-A-570 799 which is believed to correspond to U.S. Pat. No. 5,449,818 the disclosure of which is herein incorporated by reference. Advantages of this process as compared with liquid-phase phosgenation, which is otherwise conventional, are the energy saving resulting from the minimization of an expensive solvent and phosgene circuit. Solvents are generally also used in gas-phase phosgenation, but in smaller amounts than in liquid-phase phosgenation, as described, for example, in DE-A-10245704 which is believed to correspond to U.S. Pat. No. 6,800,781, the disclosure of which is herein incorporated by reference. Thus, in this case of gas phase phosgenation, the object is also, in principle the separation of phosgene, hydrogen chloride and solvent.

There are suitable as organic amines for the present process, in principle, any primary amines having one or more primary amino groups which are able to react with phosgene to form one or more isocyanates having one or more isocyanate groups. The suitable amines have at least one, preferably two, or optionally three or more, primary amino groups.

For example, there are suitable as organic primary amines the aliphatic, cycloaliphatic, aliphatic-aromatic, aromatic amines, diamines and/or polyamines, such as, for example, methylamine, ethylamine, butylamine, stearylamine, aniline, halo-substituted phenylamines, e.g. 4-chlorophenylamine, 1,4-diaminobutane, 1,6-diaminohexane, 1,8-diaminooctane, 1-amino-3,3,5-trimethyl-5-amino-cyclohexane, lysine ethyl ester, lysine aminoethyl ester, 1,6,11-triaminoundecane or 1,5- and/or 1,8-naphthylenediamine, 1,4-diaminobenzene, p-xylylenediaamine, perhydrogenated 2,4- and/or 2,6-diaminotoluene, 2,2'-, 2,4'- and/or 4,4'-diaminodicyclohexylmethane, 2,4-, 2,6-diaminotoluene or mixtures thereof, 4,4'-, 2,4'- or 2,2'-diphenylmethanediamine or mixtures thereof, as well as higher molecular weight isomeric, oligomeric or polymeric derivatives of the mentioned amines and polyamines. Other possible amines are known from the prior art. Preferred amines for the present invention are the di- and poly-amines of the diphenylmethane series (MDA, monomeric, oligomeric and polymeric amines), 2,4-, 2,6-diaminotoluene (TDA, toluenediamines), for example technical mixtures of 2,4-, and 2,6-diaminotoluene (TDA, toluenediamines) in the weight ratio 80:20, isophoronediamine and hexamethylenediamine. In the phosgenation reaction, the corresponding isocyanates are obtained: for example, di- and poly-isocyanates of the diphenylmethane series (i.e. MDI: monomeric, oligomeric and polymeric isocyanates), toluene diisocyanate (TDI), hexamethylene diisocyanate (HDI) and isophorone diisocyanate (IPDI).

The amines can be reacted with phosgene in a one-stage or two-stage or optionally multi-stage reaction. Both a continuous and a discontinuous procedures are possible.

If a single-stage phosgenation in the gas phase is chosen, the reaction is carried out at a temperature above the boiling temperature of the amine, preferably in a mean contact time of from 0.5 to 5 seconds and at temperatures of from 200 to 600° C.

In the case of phosgenation in the liquid phase, temperatures of from 20 to 240° C. and pressures of from 1 to about 50 bar absolute are conventionally used. The phosgenation in the liquid phase can be carried out in one stage or in a plurality of stages, with it being possible for phosgene to be used in stoichiometric excess. The amine solution and the phosgene solution are preferably combined by means of a static mixing element and then guided through one or more reaction towers, for example, from bottom to top, where the mixture reacts completely to give the desired isocyanate. In addition to reaction towers provided with suitable mixing elements, it is also possible to use reaction containers having a stirring device. In addition to static mixing elements, special dynamic mixing elements can also be used. Suitable static and dynamic mixing elements are known from the prior art (EP 0830894 A 1 which is believed to correspond to U.S. Pat. No. 5,931,579, the disclosure of which is herein incorporated by reference, EP 0291820 A1 which is believed to correspond to U.S. Pat. No. 4,915,509, the disclosure of which is herein incorporated by reference).

Continuous liquid-phase isocyanate preparation on an industrial scale is generally carried out in two stages. In the first stage, generally at temperatures of not more than 220° C., preferably not more than 160° C., carbamoyl chloride is formed from amine and phosgene, and amine hydrochloride is formed from amine and cleaved hydrogen chloride. This first stage is highly exothermic. In the second stage, the carbamoyl chloride is cleaved to isocyanate and hydrogen chloride, and the amine hydrochloride is reacted to give carbamoyl chloride. The second stage is generally carried out at temperatures of at least 90° C., preferably from 100 to 240° C.

After the process step of amine phosgenation, the isocyanates formed in the phosgenation are generally separated off. This is effected, for example, by first separating the reaction mixture of the phosgenation into a liquid product stream and a gaseous product stream. Processes suitable therefore, such as condensation or washing, are generally known and are described, for example, in U.S. Pat. No. 3,544,611, the disclosure of which is herein incorporated by reference, and GB-A-827376, the disclosure of which is herein incorporated by reference. The liquid product stream contains substantially the isocyanate or isocyanate mixture, solvent that has optionally been used, and also a small portion of unreacted phosgene. The gaseous product stream consists substantially of hydrogen chloride gas, excess phosgene, amounts of solvent corresponding to the thermodynamic equilibrium, and also secondary products from the phosgene production, such as, for example, carbon dioxide. Further separation of residual amounts of phosgene is optionally carried out by further working up of the liquid product stream.

It is therefore desirable, especially from an economic point of view, to recover excess phosgene as completely as possible for further use in the phosgenation, to reduce the solvent circuit to an economically expedient minimum and to isolate hydrogen chloride that is as pure as possible for further use.

Separation of the solvent from the liquid product stream by distillation, its purification and return to the stage of the amine phosgenation can be carried out according to one of the processes known from the prior art such as is described in, for example, DE-A-102006022448 (and citations contained therein), which is believed to correspond to U.S. Published Patent Application 20070265456, the disclosure of which is herein incorporated by reference.

The gaseous stream containing hydrogen chloride, phosgene, solvent, and low boilers and inert substances, which is conventionally obtained in the reaction of aliphatic or aromatic amines with phosgene to give the corresponding isocyanates in step a) in the liquid-phase phosgenation, preferably contains from 20 to 75 wt. % phosgene, from 5 to 50 wt. % solvent and from 5 to 50 wt. % hydrogen chloride, based on the weight of the stream. The breadth of variation in the composition of the stream containing hydrogen chloride, phosgene, solvent, and low boilers and inert substances arises because it is possible to use different processes for the phosgenation, in which the processes are characterised by different pressures, temperatures and process solvents, or the phosgenation can optionally be carried out in the gas phase or without a solvent.

Stripping of the condensation product obtained in step b), which consists substantially of solvent, hydrogen chloride and phosgene, is carried out in the process according to the invention in step c) in a stripping column. This is usually a column consisting of a stripping part (i.e. feed takes place at the top of the column) and a bottom evaporator, which is usually in the form of a natural circulation evaporator, a forced circulation evaporator or a falling-film evaporator. The addition of an additional stripping agent is possible; however, it is preferred not to add a stripping agent, with the phosgene and hydrogen chloride evaporated in the bottom of the stripping column serving as stripping agent. On an industrial scale, the column body preferably has a diameter of from 0.1 to 4.0 m, and preferably from 0.5 to 2.0 m. The region of the column that is equipped with material-exchange internals is usually, depending on the type, from 1.0 to 10.0 m, preferably from 2.0 to 8.0 m, and more preferably from 4.0 to 6.0 m.

As internals for providing as large a material exchange surface as possible there can be used any fillers, packings or material exchange trays known from the prior art and known to the person skilled in the art. These can be conventional types of packing, such as, for example, B1, C1 (Montz) or Mellapak, Kerapak (Sulzer) or Ralupak (Raschig) or Rombopak (Kühni), or any other conventional types of packing for rectification or types of filler (all from VFF unless specified otherwise) such as, for example, Raschig rings, Pall rings or saddles of the type Intalox, Berl, Super-Torus (Raschig) or Super, Interpack, Top-Pak, Hacketten, Igel, VSP or Hiflow ring (Rauschert) in the commercially available sizes and made of the materials known to the person skilled in the art that are resistant to the substance system under the prevailing conditions. The introduction of the feed at the top of the stripping column to the filler or packing can preferably be carried out via a liquid distributor according to the prior art. In the case of material exchange trays, the feed can be introduced via a feed tray according to the prior art. The absolute pressure at the top of the stripping column is necessarily given by the pressure at the top of the absorption column that is used and the pressure losses that occur in the column, and is accordingly, preferably from 1 to 35 bar, and more preferably from 1.2 to 3 bar. The bottom temperature, according to the pressure loss in the column and the solvent used, is preferably from 130 to 410° C., and more preferably from 135 to 230° C. The solvent stream (solvent phase) from the bottom of the stripper has a phosgene concentration of <0.1 wt. %, preferably <0.01 wt. %, and more preferably <0.001 wt. %, based on the liquid solvent stream (solvent phase).

The return of the solvent phase obtained in step c) into the phosgenation in step a), which is the subject of step d), can be in such a manner that the entirety of the solvent phase obtained in step c) is returned. However, it is also possible to return only a portion of the solvent phase obtained in step c). Preferably more than 10%, more preferably more than 50%, most preferably from 60 to 100%, and most especially preferably from 65 to 99.95%, of the solvent phase obtained in step c) is returned to the phosgenation reaction in step a).

The invention is now explained in detail below with reference to FIGS. 1-3.

FIG. 1 is a diagrammatic representation of the separation of the gaseous stream containing hydrogen chloride, phosgene, solvent, and low boilers and inert substances, in a combination of a single- or multi-stage partial condensation, followed by stripping of the resulting condensation product, and further separation of the vapor stream in an absorption column.

Figure 2:
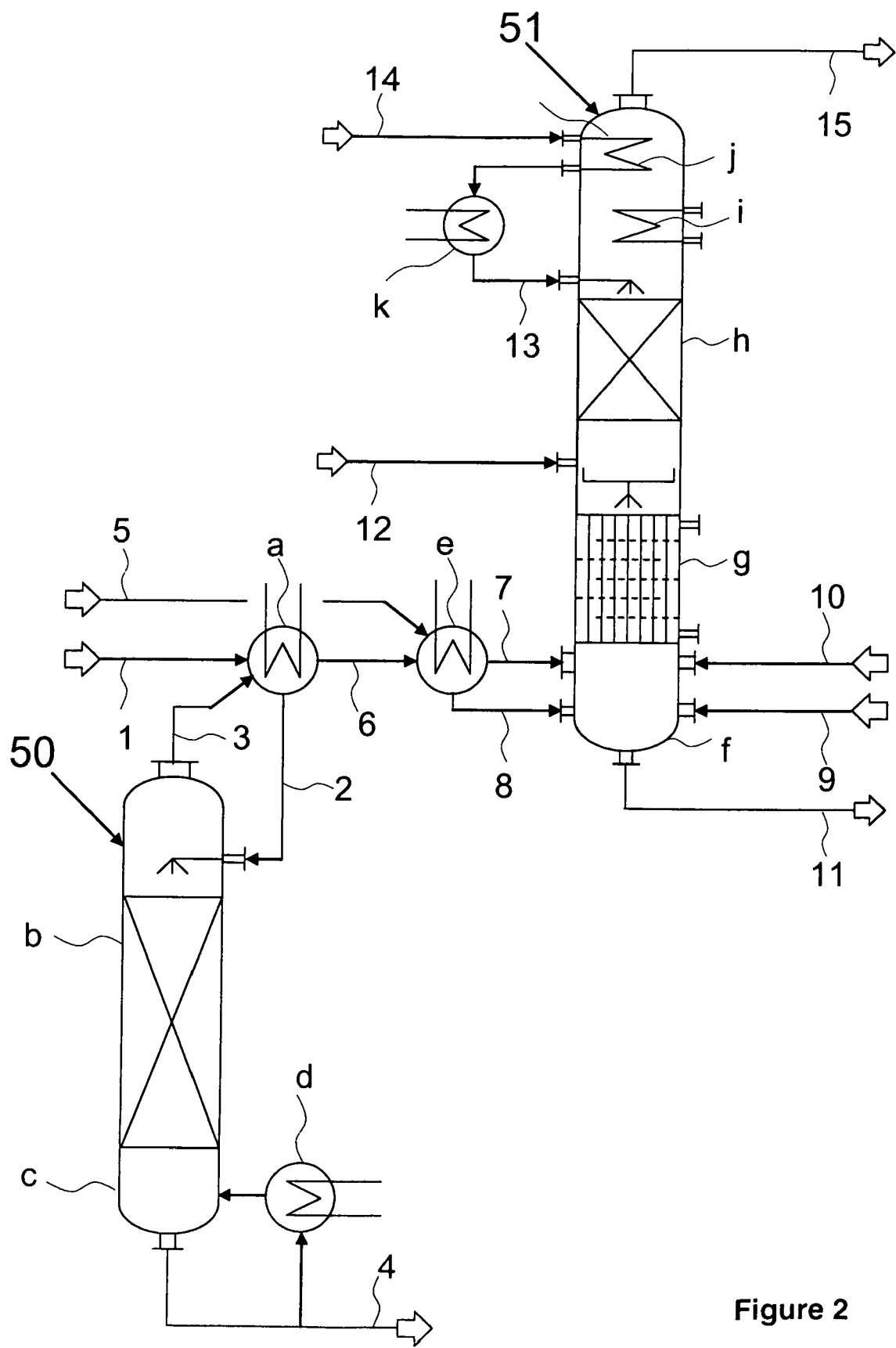
FIG. 2 A diagrammatic representation of the separation of the gaseous stream containing hydrogen chloride, phosgene, solvent, and low boilers and inert substances, in a combination of a single- or multi-stage partial condensation, followed by stripping of the resulting condensation product, and further single- or multi-stage partial condensation at a correspondingly lower temperature than in the partial condensation upstream of the stripping column, and further separation of the vapor stream in an absorption column.

FIG. 2 is a diagrammatic representation of the separation of the gaseous stream containing hydrogen chloride, phosgene, solvent, and low boilers and inert substances, in a combination of a single- or multi-stage partial condensation, followed by stripping of the resulting condensation product, and further single- or multi-stage partial condensation at a correspondingly lower temperature than in the partial condensation upstream of the stripping column, and further separation of the vapor stream in an absorption column.

Figure 3:
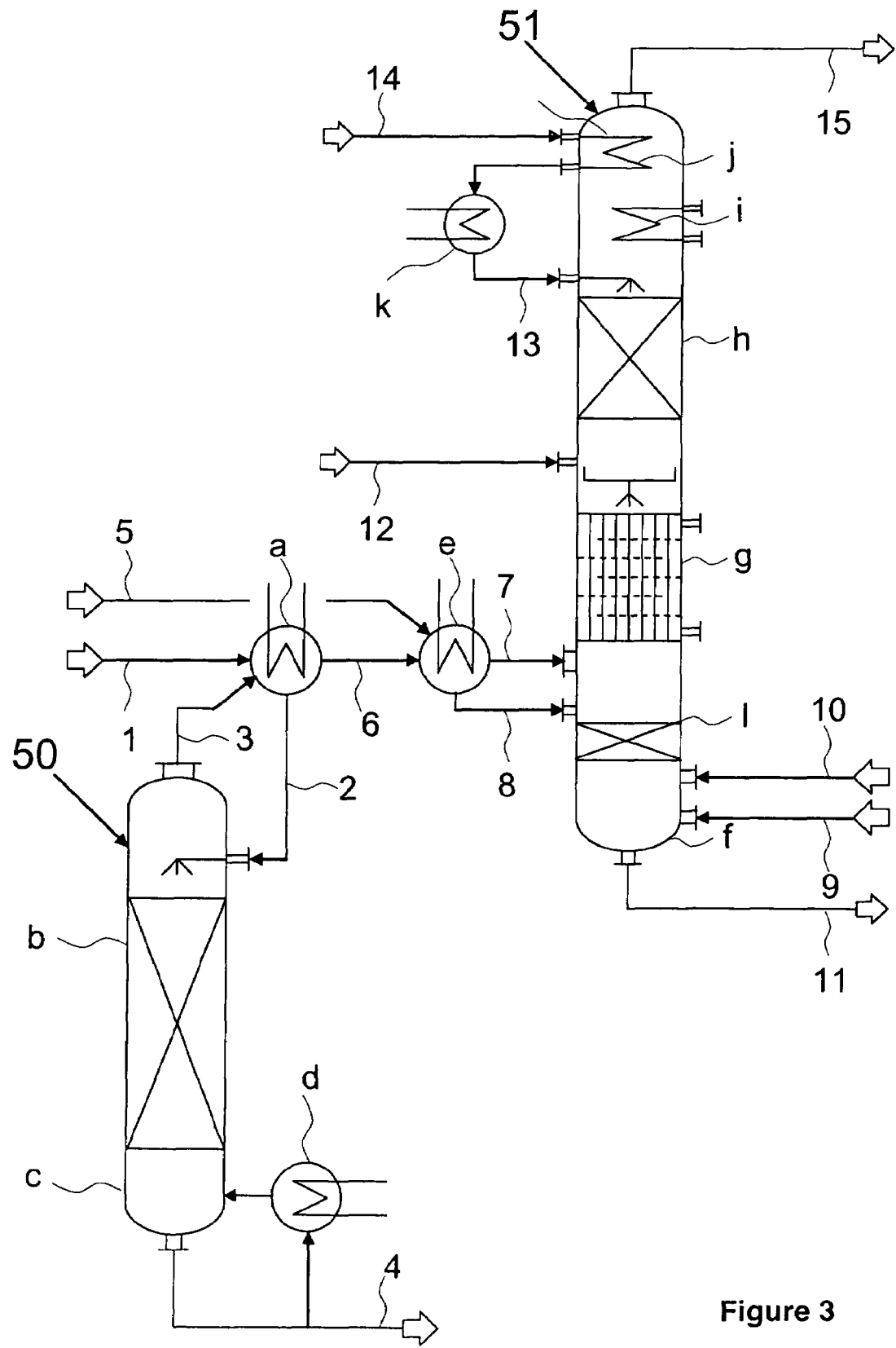
FIG. 3 a diagrammatic representation of the separation of the gaseous stream containing hydrogen chloride, phosgene, solvent, and low boilers and inert substances, in a combination of a single- or multi-stage partial condensation, followed by stripping of the resulting condensation product, and further single- or multi-stage partial condensation at a correspondingly lower temperature than in the partial condensation upstream of the stripping column, and further separation of the vapor stream in an absorption column and also stripping of the phosgene solution.

FIG. 3 is a diagrammatic representation of the separation of the gaseous stream containing hydrogen chloride, phosgene, solvent, and low boilers and inert substances, in a combination of a single- or multi-stage partial condensation, followed by stripping of the resulting condensation product, and further single- or multi-stage partial condensation at a correspondingly lower temperature than in the partial condensation upstream of the stripping column, and further separation of the vapor stream in an absorption column and also stripping of the phosgene solution.

More specifically, FIG. 1 illustrates a diagrammatic representation of the separation of the gaseous stream containing hydrogen chloride, phosgene, solvent, and low boilers and inert substances, in a combination of a single- or multi-stage partial condensation (i.e. step b) of the claimed process), followed by stripping of the resulting condensation product (i.e. step c) of the claimed process), and further separation of the vapor stream in an absorption column (i.e. step e) of the claimed process).

In a preferred embodiment of the invention, the gaseous stream 1 containing hydrogen chloride, phosgene, solvent, and low boilers and inert substances, which is conventionally obtained in the reaction of aliphatic or aromatic amines with phosgene to give the corresponding isocyanates, is first passed, for separation, into a single- or multi-stage partial condensation a. Phosgene-containing solvent streams 5 from the isocyanate process, as can conventionally be obtained as washing liquids from the phosgene preparation, ring liquids from the vacuum system, condensation products from the solvent distillation, etc., can additionally be supplied there. Suitable heat exchangers are any condensers according to the prior art. The condensation step is usually carried out with air-cooled cooling brine, preferably at from 25 to 50° C., and more preferably from 30 to 40° C. The condensation product 2 formed thereby is introduced as feed at the top of a stripping column 50. The feed is separated in the structured packing part b of the column into a top vapor stream 3, which has been depleted of solvent to the greatest possible extent and is passed into the first partial condensation stage a again, and a solvent stream 4, which has been freed of phosgene to the greatest possible extent, at the bottom c of the column. The vapors necessary therefore are produced from the liquid flowing from the packing b by the bottom evaporator d.

The vapor stream 6 from the first partial condensation stage a is passed for further separation into a phosgene absorption column 51, a combination of isothermal absorption g and adiabatic absorption h with after-condensation i of the solvent and the recovery of energy j from the hydrogen chloride stream, which contains only small amounts of phosgene or solvent. In addition, condensed phosgene 9 and non-condensable residual phosgene 10 from the phosgene preparation, which has optionally for the most part been recovered by a washing column in chlorobenzene, is introduced at the bottom f of the absorption column 51. The feed 12 at the top of the isothermal absorption g consists of solvent, which can optionally also be replaced by solvent streams which are contaminated with small amounts of phosgene (such as, for example, washing liquids from the phosgene preparation, ring liquids from the vacuum system, condensation products from the solvent distillation, etc.). Cooling of the isothermal absorption is preferably carried out with cold brine, preferably at temperatures from −40 to +0° C., and more preferably at temperatures from −20 to −10° C.

The hydrogen chloride stream prepurified by the isothermal absorption g is fed internally to the adiabatic absorption stage h and is further freed of phosgene therein. For the absorption, solvent 13, which has been cooled by the heat exchanger k with cold brine to temperatures of preferably from −50 to +0° C., and more preferably from −40 to −20° C., is introduced counter-currently as stream 14 at the top of the adiabatic absorption h. The hydrogen chloride stream 15, which has been freed of phosgene in the adiabatic absorption h and of solvent in the after-condensation i, leaves at the top of the absorption column 51. Cooling in the after-condensation is carried out with cold brine at temperatures preferably from −50 to +0° C., and more preferably from −40 to −20° C.

In order to recover energy, the solvent stream 13 is precooled in the heat exchanger j and the hydrogen chloride stream 15 is heated.

A concentrated phosgene solution 11 is drawn off at the bottom f of the phosgene absorption column and fed back into the reaction stage.

FIG. 2 illustrates a diagrammatic representation of the separation of the gaseous stream containing hydrogen chloride, phosgene, solvent, and low boilers and inert substances, in a combination of a single- or multi-stage partial condensation (i.e. step b) of the process herein), followed by stripping of the resulting condensation product (i.e. step c) of the process herein) and further single- or multi-stage partial condensation at a correspondingly lower temperature than in the partial condensation upstream of the stripping column, and further separation of the vapor stream in an absorption column (i.e. step e) of the process herein).

In a preferred embodiment of the invention, the gaseous stream 1 containing hydrogen chloride, phosgene, solvent, and low boilers and inert substances, which is conventionally obtained in the reaction of aliphatic or aromatic amines with phosgene to give the corresponding isocyanates, is first passed, for separation, into a single- or multi-stage partial condensation a. Phosgene-containing solvent streams 5 from the isocyanate process, as can conventionally be obtained as washing liquids from the phosgene preparation, ring liquids from the vacuum system, condensation products from the solvent distillation, etc., can additionally be supplied there or in the partial condensation stage e downstream of the stripping column. Suitable heat exchangers are any condensers according to the prior art. The condensation step is usually carried out with air-cooled cooling brine, preferably at temperatures of from 25 to 50° C., and more preferably from 30 to 40° C. The condensation product 2 formed thereby is introduced as feed at the top of a stripping column 50. The feed is separated in the structured packing part b of the column into a top vapor stream 3, which has been depleted of solvent to the greatest possible extent and is passed into the first partial condensation stage a again, and a solvent stream 4, which has been freed of phosgene to the greatest possible extent, at the bottom c of the column. The vapors necessary therefore are produced from the liquid flowing from the packing b by the bottom evaporator d.

The vapor stream 6 from the first partial condensation stage a is passed via a second single- or multi-stage partial condensation e which is operated at a lower temperature than the condensation stage a. Suitable heat exchangers are any condensers according to the prior art. The condensation step is preferably carried out with cold brine at temperatures preferably from −40 to +10° C., and more preferably from −20 to −10° C. The resulting vapor stream 7 and condensation product stream 8 are passed for further separation into a phosgene absorption column 51, a combination of isothermal absorption g and adiabatic absorption h with after-condensation i of the solvent and the recovery of energy j from the hydrogen chloride stream, which contains only small amounts of phosgene or solvent. In addition, condensed phosgene 9 and noncondensable residual phosgene 10 from the phosgene preparation, which has optionally for the most part been recovered by a washing column in chlorobenzene, is introduced at the bottom f of the absorption column 51. The feed 12 at the top of the isothermal absorption g consists of solvent, which can optionally also be replaced by solvent streams which are contaminated with small amounts of phosgene (such as, for example, washing liquids from the phosgene preparation, ring liquids from the vacuum system, condensation products from the solvent distillation, etc.). Cooling of the isothermal absorption is preferably carried out with cold brine preferably at temperatures from −40 to +0° C., and more preferably at temperatures from −20 to −10° C.

The hydrogen chloride stream prepurified by the isothermal absorption g is fed internally to the adiabatic absorption stage h and is further freed of phosgene therein. For the absorption, solvent 13, which has been cooled by the heat exchanger k with cold brine to temperatures of preferably from −50 to +0° C., and more preferably from −40 to −20° C., is introduced counter-currently as stream 14 at the top of the adiabatic absorption h. The hydrogen chloride stream 15, which has been freed of phosgene in the adiabatic absorption h and of solvent in the after-condensation i, leaves at the top of the absorption column 51. Cooling in the after-condensation is carried out with cold brine preferably at temperatures from −50 to +0° C., and more preferably at temperatures from −40 to −20° C. In order to recover energy, the solvent stream 13 is precooled in the heat exchanger j and the hydrogen chloride stream 15 is heated.

A concentrated phosgene solution 11 is drawn off at the bottom f of the phosgene absorption column and fed back into the reaction stage.

In particular FIG. 3, illustrates a diagrammatic representation of the separation of the stream containing hydrogen chloride, phosgene, solvent, and low boilers and inert substances in a combination of a single- or multi-stage partial condensation (i.e. step b) of the process herein), followed by stripping of the resulting condensation product (i.e. step c) of the process herein), and further single- or multi-stage partial condensation at a correspondingly lower temperature than in the partial condensation upstream of the stripping column, and further separation of the vapor stream in an absorption column (i.e. step e) of the process herein), and also stripping of the phosgene solution.

In the embodiment of the process as shown in FIG. 3, the purity of the liquid phosgene stream 11 (phosgene solution), which is drawn off at the bottom of the absorption column 51, in particular in respect of low boilers, which are soluble in phosgene or in the solvent, such as, for example, hydrogen chloride, can be increased again.

In a preferred embodiment of the invention, the gaseous stream 1 containing hydrogen chloride, phosgene, solvent, and low boilers and inert substances, which is conventionally obtained in the reaction of aliphatic or aromatic amines with phosgene to give the corresponding isocyanates, is first passed, for separation, into a single- or multi-stage partial condensation a. Phosgene-containing solvent streams 5 from the isocyanate process, as can conventionally be obtained as washing liquids from the phosgene preparation, ring liquids from the vacuum system, condensation products from the solvent distillation, etc., can additionally be supplied there or in the partial condensation stage e downstream of the stripping column. Suitable heat exchangers are any condensers according to the prior art. The condensation step is usually carried out with air-cooled cooling brine, preferably at temperatures from 25 to 50° C., and more preferably at temperatures from 30 to 40° C. The condensation product 2 formed thereby is introduced as feed at the top of a stripping column 50. The feed is separated in the structured packing part b of the column into a top vapor stream 3, which has been depleted of solvent to the greatest possible extent and is passed into the first partial condensation stage a again, and a solvent stream 4, which has been freed of phosgene to the greatest possible extent, at the bottom c of the column. The vapors necessary therefore are produced from the liquid flowing from the packing b by the bottom evaporator d.

The vapor stream 6 from the first partial condensation stage a is passed via a second single- or multi-stage partial condensation e which is operated at a lower temperature. Suitable heat exchangers are any condensers according to the prior art. The condensation step is preferably carried out with cooling brine, preferably at temperatures from −40 to +10° C., and more preferably at temperatures from −20 to −10° C. The resulting vapor stream 7 and condensation product stream 8 are passed for further separation into a phosgene absorption column 51, a combination of isothermal absorption g and adiabatic absorption h with after-condensation i of the solvent and the recovery of energy j from the hydrogen chloride stream, which contains only small amounts of phosgene or solvent. In addition, condensed phosgene 9 and an uncondensed phosgene stream 10, which also still contains inert gases typical for phosgene, from the phosgene preparation, is introduced at the bottom f of the absorption column 51. The feed 12 at the top of the isothermal absorption g consists of solvent, which can optionally also be replaced by solvent streams which are contaminated with small amounts of phosgene (such as, for example, washing liquids from the phosgene preparation, ring liquids from the vacuum system, condensation products from the solvent distillation, etc.). Cooling of the isothermal absorption is preferably carried out with cold brine preferably at temperatures from −40 to +0° C., and more preferably at temperatures from −20 to −10° C.

The hydrogen chloride stream prepurified by the isothermal absorption g is fed internally to the adiabatic absorption stage h and is further freed of phosgene therein. For the absorption, solvent 13, which has been cooled by the heat exchanger k with cold brine to temperatures of preferably from −50 to +0° C., and more preferably from −40 to −20° C., is introduced counter-currently as stream 14 at the top of the adiabatic absorption h. The hydrogen chloride stream 15, which has been freed of phosgene in the adiabatic absorption h and of solvent in the after-condensation (i), leaves at the top of the absorption column 51. Cooling in the after-condensation is carried out with cold brine preferably at temperatures from −50 to +0° C., and more preferably at temperatures from −40 to −20° C. In order to recover energy, the solvent stream 13 is precooled in the heat exchanger j and the hydrogen chloride stream 15 is heated.

The phosgene solution which flows from the partial condensation e and the isothermal absorption g and which still contains low boilers is stripped in the packing part 1 by the counter-current gaseous phosgene stream 10, which also contains inert gases typical for phosgene preparation.

The construction of the stripping section l corresponds to the known prior art. It is designed in view of the desired low boiler content in the bottom stream, in a manner known to the person skilled in the art and as is conventional for such separations. The apparatus-related design can be a packing, filler or tray column section.

A concentrated phosgene solution 11 is drawn off at the bottom f of the phosgene absorption column and fed back into the reaction stage.

In the embodiment of the present invention shown in FIG. 3, the concentration of hydrogen chloride and other low boilers in the phosgene solution (liquid phosgene stream) can be reduced further by the stripping part 1 arranged beneath the isothermal absorption g, without requiring an additional separate column with additional heat exchangers, by using a phosgene-containing vapor stream from the phosgene preparation of the isocyanate synthesis (i.e. a stream containing at least 50 wt. % phosgene, based on the weight of the stream) as stripping gas and condensing it during the stripping. This vapor stream is conventionally liquefied in the isocyanate synthesis in a separate condensation and then added to the phosgene solution. In the process according to the invention, the condensation is optionally carried out by means of the latent heat of the phosgene solution flowing from the isothermal absorption.

EXAMPLES a) The preparation of isocyanate and the separation, carried out thereby, of a stream containing hydrogen chloride, phosgene, solvent, and low boilers and inert substances, which is formed in the reaction of aliphatic or aromatic amines with phosgene to give the corresponding isocyanates in a reaction stage corresponding to the prior art, is carried out by the process according to the invention. The separation is thereby carried out by a two-stage partial condensation, wherein the condensation product from the first stage of the partial condensation is introduced as feed at the top of a stripping column, the bottom product of the stripping column is fed back to the fresh solvent tank, and the top vapors of the stripping column are passed back into the first stage of the partial condensation again, and the totality of the vapors from the first partial condensation are fed into the second partial condensation, subsequent partial isothermal absorption of the phosgene with chlorobenzene, counter-currently, followed by adiabatic absorption of the remaining phosgene with chlorobenzene, counter-currently, and finally by after-condensation of the residual chlorobenzene from the low-phosgene and low-solvent hydrogen chloride stream. Such a process is as described above with respect to FIG. 2.

The condensed phosgene and the non-condensable residual phosgene from the phosgene preparation, recovered by a washing column in chlorobenzene, are likewise passed into the bottom of the absorption column. The concentrated phosgene solution thereby obtained at the bottom is returned to the reaction stage again for reaction with the amine. As a result of this cyclic procedure, the hydrogen chloride stream to be separated is obtained again in its original composition and amount.

The gaseous hydrogen chloride stream 1 from the reaction stage of 39.1 kg/h is fed into the heat exchanger of the first partial condensation stage a, which is operated at 45° C. (cooling brine). The hydrogen chloride stream 1 contains 23.8 wt. % hydrogen chloride, 49.3 wt. % chlorobenzene, 26.9 wt. % phosgene and small amounts of the low boilers typical for an isocyanate synthesis. The low boilers are not mentioned explicitly each time in the following compositions of the substance streams. The condensation product 2 formed thereby of 20.4 kg/h (0.7 wt. % hydrogen chloride, 9.7 wt. % phosgene, 89.6 wt. % chlorobenzene) is introduced as feed at the top of a stripping column 50. The structured packing part b of the column has a height of 2 m, and the column has a diameter of 55 mm. The top vapors 3 of the stripping column 50 of 2.3 kg/h (5.8 wt. % hydrogen chloride, 86.5 wt. % phosgene, 7.7 wt. % chlorobenzene) are passed into the first partial condensation stage a again. The liquid flowing from the packing b is collected in the bottom c of the stripping column 50 and partially evaporated by the bottom evaporator d or discharged as purified chlorobenzene bottom stream 4. 18.1 kg/h of purified chlorobenzene having a residual phosgene content of about 10 ppm are thereby obtained.

The vapor stream 6 from the first partial condensation stage a of 21.0 kg/h (44.4 wt. % hydrogen chloride, 50.2 wt. % phosgene, 5.4 wt. % chlorobenzene) is guided into the subsequent second partial condensation stage e, which is operated at −17° C. (cold brine). The addition of liquid phosgene-containing chlorobenzene 5 from the vacuum system as shown in FIG. 2 was not carried out in the example.

The subsequent combination of isothermal and adiabatic absorption with after-condensation of the solvent from the waste gas is carried out in this example in a combination of a plurality of apparatuses which were connected as though the steps carried out were arranged within a column body.

The vapor stream 7 of 14.8 kg/h and −16.5° C. (61.55 wt. % hydrogen chloride, 38.4 wt. % phosgene, 0.05 wt. % chlorobenzene) and the stream of condensation product 8 of 6.2 kg/h and −16.5° C. (3.7 wt. % hydrogen chloride, 78.0 wt. % phosgene, 18.3 wt. % chlorobenzene) are fed beneath the isothermal absorption stage g into the bottom f of the phosgene absorption column. In addition, the condensed phosgene 9 of 11.2 kg/h (0.3 wt. % hydrogen chloride, 99.7 wt. % phosgene) and the non-condensable residual phosgene 10, which was recovered for the most part by a washing column in chlorobenzene, of 1.1 kg/h (0.4 wt. % hydrogen chloride, 19.4 wt. % phosgene, 80.2 wt. % chlorobenzene) from the phosgene preparation are fed into the bottom f of the absorption column 51. For the isothermal absorption, a vertical heat exchanger with a tube was used. Cooling is effected with cold brine at −17° C. The tube has a diameter of 54.4 mm, a length of 3 m and is packed with 15×15 mm Pall rings. The feed 12 at the top of the isothermal absorption g consists of chlorobenzene in an amount of 3.7 kg/h and at a temperature of −38° C. Furthermore, there is the internal liquid reflux from the packing of the adiabatic absorption column h in the isothermal absorption step. The hydrogen chloride stream prepurified by the isothermal absorption g is fed to the adiabatic absorption stage h. The resulting phosgene solution 11 of 43.2 kg/h and −6° C. (2.1 wt. % hydrogen chloride, 50.8 wt. % phosgene, 41.7 wt. % chlorobenzene) is fed back into the reaction stage.

The adiabatic absorption is carried out in a packed column h having a diameter of 55 mm. The packed height is 2 m. For the absorption, 14.9 kg/h of chlorobenzene 14, which has been cooled to −30° C. by the heat exchanger k operated with cold brine (−35° C.), and the internal condensation product stream from the after-condensation i, which is operated with cold brine at −35° C., are introduced counter-currently at the top of the adiabatic absorption h. The hydrogen chloride stream 15 of 8.5 kg/h, which has been freed of phosgene in the adiabatic absorption h and of chlorobenzene in the after-condensation i, consists of 99.5 wt. % hydrogen chloride, 0.05 wt. % chlorobenzene, 0.4 wt. % phosgene and 0.05 wt. % of the low boilers typical for an isocyanate synthesis. The pressure at the top is 1.45 bar absolute, the temperature at the top is −34° C. Recuperative reheating of the hydrogen chloride stream 15 by the chlorobenzene 14 to be cooled, as shown in FIG. 2, was not carried out in the example.

b) In order to check the effectiveness of the stripping column in increasing the phosgene solution concentration 11 with simultaneously low phosgene losses via the hydrogen chloride stream 15 at the top of the absorption column 51, Example a) is carried out in cyclic mode under the same boundary conditions but without operating the stripping column. The condensation product 2 from the first partial condensation stage a is accordingly introduced together with the vapors 6 into the second partial condensation stage e. With the same amount of amine solution and concentration and the same process parameters in the reaction and the absorption, and with the same residual phosgene amount in the hydrogen chloride stream 15 at the top of the absorption column 51, there is obtained a phosgene solution 11 of only 60.6 kg/h (2.6 wt. % hydrogen chloride, 61.2 wt. % chlorobenzene, 36.2 wt. % phosgene).

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of isocyanates, comprising the following steps:
   a) reacting at least one amine with phosgene in the presence of a solvent, thus forming a liquid stream which contains the corresponding isocyanate and optionally solvent, and a gaseous stream which contains hydrogen chloride, phosgene, solvent, low boilers and inert substances,
   b) separating the gaseous stream which contains hydrogen chloride, phosgene, solvent, low boilers and inert substances, by partial condensation, thus forming a liquid phase and a gaseous phase, wherein said liquid phase which is guided to the top of a stripping column consists substantially of solvent, phosgene and hydrogen chloride, and said gaseous stream contains substantially hydrogen chloride, phosgene, low boilers and inert substances, and no more than 30 wt. %, based on the weight of the gaseous steam, of solvent,
   c) separating said liquid phase introduced into the stripping column in step b) which consists substantially of solvent, phosgene and hydrogen chloride, into a solvent phase and a gas phase, in which said solvent phase is removed in liquid form from the bottom of said stripping column and which has a phosgene concentration of <0.1 wt. %, based on the weight of the liquid bottom stream, and said gas phase is removed at the top of the column and contains phosgene, hydrogen chloride, low boilers, inert substances and less than 30 wt. %, based on the weight of the gas phase, of solvent,
   d) returning said solvent phase formed in step c) to said phosgenation reaction in step a),
   e) introducing said gas phase obtained in step c) into an absorption in which the phosgene present in the gas phase is absorbed in the same solvent which is used in the phosgenation reaction in step a), thereby forming a phosgene solution having a concentration of from 20 to 80 wt. % phosgene, based on the weight of said phosgene solution,
   f) optionally, mixing said phosgene solution obtained in step e) with additional phosgene, to form a concentrated phosgene solution,
   and
   g) returning said phosgene solution formed in step e) or said concentrated phosgene solution formed in step f) to the phosgenation reaction in step a).

2. The process of claim 1, in which in step e) said gas phase is partially condensed one or more times before it is introduced into said absorption.

3. The process of claim 1, additionally comprising:
   h) combining said gaseous streams formed in steps b), c) and e) to form a hydrogen chloride stream containing phosgene in a concentration of not more than 0.5 wt. %, based on the weight of the hydrogen chloride stream.

4. The process of claim 3, wherein the resultant hydrogen chloride stream contains phosgene in a concentration of not more than 0.2 wt. %, based on the weight of the hydrogen chloride stream.

5. The process of claim 3, wherein the resultant hydrogen chloride stream contains phosgene in a concentration of not more than 0.1 wt. %, based on the weight of the hydrogen chloride stream.

6. The process of claim 1, in which a) said phosgenation reaction is carried out in the liquid phase.

7. The process of claim 6, in which at least part of the amine is first mixed with said solvent phase which is being returned in step d), and the resultant amine solution is then introduced into said phosgenation reaction in step a).

8. The process of claim 6, in which at least part of the phosgene is first mixed with said solvent phase which is being returned in step d), and the resultant phosgene solution is then introduced into said phosgenation reaction in step a).

* * * * *